United States Patent
Belli

(10) Patent No.: US 7,378,085 B2
(45) Date of Patent: May 27, 2008

(54) LONG-RETENTION HAIRSTYLING GEL

(75) Inventor: Emmanuelle Belli, Asnières (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/966,751

(22) Filed: Oct. 1, 2001

(65) Prior Publication Data

US 2002/0061320 A1 May 23, 2002

(30) Foreign Application Priority Data

Oct. 2, 2000 (FR) .................... 00 12515

(51) Int. Cl.
*A61K 8/19* (2006.01)
*A61K 8/58* (2006.01)
*A61Q 5/04* (2006.01)

(52) U.S. Cl. .................... 424/70.4; 424/401

(58) Field of Classification Search ............... 424/70.4, 424/401
See application file for complete search history.

(56) References Cited

U.S. PATENT DOCUMENTS 5,612,397 A * 3/1997 Gebhard et al. ............. 524/35

5,986,015 A * 11/1999 Midha et al.

FOREIGN PATENT DOCUMENTS

WO  WO 00/40628  7/2000

OTHER PUBLICATIONS

Merck Index, 11th ed., 1989, monograph 4486.*

* cited by examiner

*Primary Examiner*—San-Ming Hui
(74) *Attorney, Agent, or Firm*—Steptoe & Johnson LLP

(57) ABSTRACT

The invention relates to cosmetic compositions, and in particular hairstyling gels, containing in a cosmetically acceptable carrier
(a) at least one fixing film-forming polymer chosen from branched block copolymers comprising, as principal monomers, at least one $C_{1-20}$ alkyl acrylate and/or at least one N-mono- or N,N-di($C_{2-12}$ alkyl)(meth)acrylamide, and acrylic acid and/or methacrylic acid,
(b) at least one thickening agent chosen from homopolymers and copolymers based on (meth)acrylic acid, which are crosslinked or noncrosslinked, and
(c) at least one cothickening agent chosen from noncellulosic thickening polymers different from (b).

20 Claims, No Drawings

LONG-RETENTION HAIRSTYLING GEL

The present invention relates to a cosmetic composition thickened by a combination of at least two thickening polymers, and the use of this composition for hairstyling.

Hairstyling gels are solutions of one or more fixing film-forming polymers thickened or gelled by one or more thickening polymers.

Although a very large number of fixing polymers are known in the hairstyling field, most of them have a fixing power which is limited over time and which is poorly resistant to moisture.

The highly advantageous hairstyling properties of a particular group of branched block copolymers were recently discovered.

These copolymers, used in hairstyling compositions, exhibit a combination of physicochemical and cosmetic properties which make them excellent fixing polymers. Thus, these block copolymers spread easily on the hair, exhibit good adhesion to the hair fibers, give a scarcely sticky feel, are easy to remove with a shampoo and give satisfactory fixing of good elasticity which is stable over time and which is particularly resistant to moisture.

An increase in the viscosity of the composition by increasing the concentration of the thickening polymer is found to be unsatisfactory because of the poor qualities of using the gel which result therefrom, such as a pasty and sticky consistency and some difficulty in spreading and applying the gel.

A need therefore exists for a thickening system capable of satisfactorily thickening or gelling a hairstyling composition based on the novel fixing copolymers indicated above.

The applicant has found, after long research work, a particular combination of thickening polymers which make it possible to overcome the problems of fluidification and alteration of the properties of using the gel which are disclosed above.

The subject of the present invention is consequently cosmetic compositions containing in a cosmetically acceptable carrier:

(a) at least one fixing film-forming polymer chosen from branched block copolymers comprising, as principal monomers, (1) at least one $C_{1-20}$ alkyl acrylate and/or at least one N-mono- or N,N-di-($C_{2-12}$) alkylacrylamide or alkylmethacrylamide, and (2) acrylic acid and/or methacrylic acid, (b) at least one thickening agent chosen from homopolymers and copolymers based on acrylic acid or methacrylic acid, which are cross-linked or non-cross-linked, and (c) at least one co-thickening agent chosen from noncellulosic thickening polymers different from thickening agent (b).

The subject of the invention is also the use of the above thickening or gelled cosmetic compositions for styling and fixing the hair.

The fixing film-forming polymer (a) used in the cosmetic compositions of the present invention is a branched block copolymer having a structure consisting of hydrophobic blocks onto which a certain number of more hydrophilic blocks are attached in particular via bifunctional units. These copolymers have at least two glass transition temperatures.

They are in particular described in published international patent application WO 00/40628 whose content forms an integral part of the present application and whose content is expressly incorporated herein by reference.

The branched block copolymers described above are provided, for example, under the names EX-SDR-26® and EX-SDR-45® by GOODRICH.

These copolymers have the following composition:
acrylic acid - 26 to 36 mol %,
n-butyl acrylate - 27.5 to 30.5 mol %,
methacrylic acid - 33.3 to 45.3 mol %, and
allyl methacrylate - 0.48 to 0.92 mol %.

The more hydrophobic blocks have a molecular weight of 10,000 to 100,000 and the more hydrophilic blocks have a molecular weight of 1000 to 100,000.

The above fixing film-forming polymers are preferably used in anionic form, that is to say in the form of a salt resulting from the partial or complete neutralization of the acrylic or methacrylic acid groups. The neutralizing agent may be any physiologically acceptable inorganic or organic base which does not interfere in a disadvantageous manner with the thickening system. There may be mentioned, by way of example of a preferred neutralizing agent, 2-amino-2-methyl-1-propanol or sodium hydroxide.

The cosmetic compositions of the present invention generally contain between 0.1 and 10% by weight, and preferably between 1 and 5% by weight, of fixing film-forming polymer relative to the total weight of the final composition.

The thickening system used in the cosmetic compositions of the present invention necessarily comprises:
(b) at least one thickening polymer based on acrylic acid or methacrylic acid, and
(c) at least one noncellulosic thickening polymer (co-thickening agent) different from the thickening polymer (b).

The thickening polymer (b) is chosen from poly(acrylic acid), poly(methacrylic acid), copolymers of acrylic acid and methacrylic acid, copolymers comprising units derived from acrylic acid and/or methacrylic acid as well as units derived from other acrylic or vinyl monomers such as $C_{1-30}$ alkyl acrylates, $C_{1-30}$ alkyl methacrylates, and vinyl acetate.

These acrylic homopolymers or copolymers may also be cross-linked.

They are used in a form which is partially or completely neutralized with a physiologically acceptable organic or inorganic base. In a preferred embodiment of the invention, the polymer (b) is a crosslinked homopolymer of methacrylic acid or of acrylic acid.

There may be mentioned by way of examples of such polymers, those marketed by GOODRICH under the names Carbopol® 940, Carbopol® 941, Carbopol® 980, Carbopol® 981, Carbopol® ETD 2001, Carbopol® ETD 2050, Carbopol® 2984, Carbopol® 5984 and Carbopol® Ultrez 10, by 3V under the names Synthalen® K, Synthalen® L and Synthalen® MS, and by the company PROTEX under the names Modarez® V1250 PX, Modarez® V2000 PX, Viscaron® A1600 PE and Viscaron® A700 PE.

In another preferred embodiment of the invention, the thickening agent (b) is a copolymer of acrylic acid or of methacrylic acid and of a $C_{10-30}$ alkyl acrylate or methacrylate.

Such copolymers are marketed, for example, by GOODRICH under the names Carbopol® 1342, Carbopol® 1382, Pemulen® TR1 and Pemulen® TR2.

The concentration of thickening agent (b) in the cosmetic compositions of the present invention is preferably between 0.1 and 3% by weight, and in particular between 0.2 and 2% by weight, relative to the total weight of the final composition.

For the production of a satisfactory thickening effect, that is to say for the production of a viscosity which is at least equal to 50 deviation units on a RHEOMAT 180 viscometer, rotor 3 (25° C., reading after 30 seconds), that is about 1.9 Pa·s, this first thickening constituent (b) should be combined with a second constituent (c) performing the role of cothickening agent.

This co-thickening agent is chosen from thickening polymers different from the thickening agents (b), excluding the cellulosic thickening polymers.

According to a preferred embodiment of the present invention, this co-thickening agent (c) is a polymer of non-cellulosic natural origin.

There may be mentioned by way of thickening polymers of natural origin which can be used as co-thickening agents guar, xanthan, scleroglucan, gelan, rhamsan and karaya gums, alginates, maltodextrin, starch and its derivatives, and carob flour, and the use in particular of guar gums such as that marketed under the name Jaguar® HP105 by RHODIA, or the xanthan gums such as those marketed under the names Keltrol® and Kelza® by MONSANTO, or under the name Rhodopol® by the company RHODIA, is preferred.

As synthetic co-thickening agents, there may be used, for example, polyethylene glycols and their derivatives, as well as the homopolymers and copolymers, cross-linked or otherwise, based on acrylamide or methacrylamide such as the homopolymers of 2-acrylamido-2-methylpropane sulphonic acid, the copolymers of acrylamide or methacrylamide and of methacryloyloxyethyltrimethylammonium chloride, or the copolymers of acrylamide and 2-acrylamido-2-methyl-propanesulphonic acid.

The concentration of the co-thickening agent in the cosmetic compositions according to the present invention is preferably between 0.05 and 2% by weight, and in particular between 0.1 and 1% by weight, relative to the total weight of the final composition.

A carrier capable of solubilizing the polymer constituents (a), (b) and (c) described above is used as cosmetically acceptable carrier in the cosmetic compositions of the present invention, and it is preferably an aqueous or aqueous-alcoholic carrier.

The cosmetic compositions of the present invention may contain, in addition, other ingredients commonly used in the cosmetic field and appropriate for the application envisaged. There may be mentioned, by way of example of such additives, for example colorants, pigments, perfumes, silicones which are volatile or otherwise, organomodified or otherwise, sunscreens, anionic, nonionic, cationic or amphoteric fixing polymers, different from those described above (such as for example polyvinylpyrrolidone), as long as they do not adversely affect the advantageous properties of the cosmetic compositions of the present invention.

The present invention is illustrated with the aid of the following example.

EXAMPLE

The aqueous-alcoholic hairstyling gels A, B and C are prepared which contain the following ingredients (in parts by weight):

|  | A | B | C |
| --- | --- | --- | --- |
| Fixing polymer[a] | 0.2 | 0.2 | 0.2 |
| Acrylic thickening polymer[b] | 1.4 | 1.4 | 1.4 |
| Noncellulosic co-thickening agent[c] | 0.3 | | |
| Cellulosic co-thickening agent[d] | | 0.3 | |
| Silicone[e] | 0.2 | 0.2 | 0.2 |
| Ethanol at 96° | 17.2 | 17.2 | 17.2 |
| 2-Amino-2-methyl-1-propanol | qs pH 7.5 | qs pH 7.5 | qs pH 7.5 |
| Water | qs 100 | qs 100 | qs 100% |
| Viscosity[f] | 2.540 | 1.480 | 1.535 |

[a] Ex-SDR-26 ®, branched block copolymer of butyl acrylate and acrylic and methacrylic acids which is marketed by GOODRICH
[b] Carbopol ® Ultrez 10, poly(acrylic acid) marketed by GOODRICH
[c] Jaguar ® HP 105, guar gum marketed by RHODIA
[d] Klucel EF ®, hydroxypropyl cellulose (on average 22 mol of ethylene oxide and 23 mol of propylene oxide) marketed by the company AQUALON
[e] Mirasil ® DMCO, polydimethylsiloxane marketed by RHODIA
[f] Viscosity expressed in Pa · s, measured at 25° C. using a rotary viscometer RHEOMAT 180, rotor No. 3, reading after 30 seconds.

a) Ex-SDR-26®, branched block copolymer of butyl acrylate and acrylic and methacrylic acids which is marketed by GOODRICH b) Carbopol® Ultrez 10, poly(acrylic acid) marketed by GOODRICH c) Jaguar® HP 105, guar gum marketed by RHODIA d) Klucel EF®, hydroxypropyl cellulose (on average 22 mol of ethylene oxide and 23 mol of propylene oxide) marketed by AQUALON e) Mirasil® DMCO, polydimethylsiloxane marketed by RHODIA This example shows that the hairstyling gel A according to the present invention possesses a substantially higher viscosity than the comparative hairstyling gel C free of co-thickening agent and containing, as sole thickening agent, an acrylic thickening polymer (Carbopol® Ultrez 10).

The comparison of the hairstyling gel A according to the present invention with the comparative hairstyling gel B containing an acrylic thickening polymer (Carbopol® Ultrez 10) combined with a cellulosic co-thickening agent (Klucel®) shows that the replacement of a cellulosic co-thickening agent with a non-cellulosic co-thickening agent spectacularly improves the viscosity of the hairstyling gel.

The invention claimed is:

1. A cosmetic composition, comprising a cosmetically acceptable carrier containing:
   (a) at least one fixing film-forming polymer that is a branched block copolymer consisting essentially of 27.5 to 30.5 mol % of n-butyl acrylate, 26 to 36 mol % of acrylic acid, 33.3 to 45.3 mol % of methacrylic acid, and 0.48 to 0.92 mol % of allyl methacrylate, the polymer having a structure comprising hydrophobic blocks onto which more hydrophilic blocks are attached via bi-functional units,
   (b) at least one thickening agent that is a cross-linked or non-cross-linked homopolymer or copolymer based on acrylic acid or methacrylic acid or acrylic and methacrylic acid, and
   (c) at least one co-thickening agent that is a non-cellulosic thickening polymer different from thickening agent (b), wherein the fixing film-forming polymer has at least two glass transition temperatures.

2. The cosmetic composition according to claim 1, wherein the concentration of fixing film-forming polymer is between 0.1 and 10% by weight relative to the total weight of the composition.

3. The cosmetic composition according to claim 2, wherein the concentration of fixing film-forming polymer is between 1 and 5% by weight relative to the total weight of the composition.

4. The cosmetic composition according to claim 1, wherein the thickening agent (b) is a cross-linked acrylic acid homopolymer.

5. The cosmetic composition according to claim 1, wherein the thickening agent (b) is a copolymer of acrylic acid or methacrylic acid and a $C_{10-30}$ alkyl acrylate or methacrylate.

6. The cosmetic composition according to claim 1, wherein the concentration of thickening agent (b) is between 0.1 and 3% by weight relative to the total weight of the composition.

7. The cosmetic composition according to claim 6, wherein the concentration of thickening agent (b) is between 0.2 and 2% by weight relative to the total weight of the composition.

8. The cosmetic composition according to claim 1, wherein the co-thickening agent (c) is of natural origin.

9. The cosmetic composition according to claim 8, wherein the co-thickening agent (c) is guar gum, xanthan gum, scleroglucan gum, gelan gum, rhamsan gum, karaya gum, an alginate, maltodextrin, starch, or carob flour.

10. The cosmetic composition according to claim 1, wherein the concentration of the co-thickening agent is between 0.05 and 2% by weight relative to the total weight of the composition.

11. The cosmetic composition according to claim 10, wherein the concentration of the co-thickening agent is between 0.1 and 1% by weight relative to the total weight of the composition.

12. A method for the styling and fixing of hair, comprising applying to the hair a cosmetic composition comprising a cosmetically acceptable carrier containing:
   (a) at least one fixing film-forming polymer that is a branched block copolymer consisting essentially of, 27.5 to 30.5 mol % of n-butyl acrylate, 26 to 36 mol % of acrylic acid, 33.3 to 45.3 mol % of methacrylic acid, and 0.48 to 0.92 mol % of allyl methacrylate, the polymer having a structure comprising hydrophobic blocks onto which more hydrophilic blocks are attached via bi-functional units, wherein the fixing film-forming polymer has at least two glass transition temperatures;
   (b) at least one thickening agent that is a homopolymer or copolymer based on acrylic acid or methacrylic acid or acrylic and methacrylic acid that is cross-linked or non-cross-linked, and
   (c) at least one co-thickening agent that is a non-cellulosic thickening polymer different from thickening agent (b), wherein the composition has a viscosity of at least about 1.9 Pa·s.

13. A cosmetic composition, comprising a cosmetically acceptable carrier containing:
   (a) at least one fixing film-forming polymer that is a branched block copolymer consisting essentially of, 27.5 to 30.5 mol % of n-butyl acrylate, 26 to 36 mol % of acrylic acid, 33.3 to 45.3 mol % of methacrylic acid, and 0.48 to 0.92 mol % of allyl methacrylate, the polymer having a structure comprising hydrophobic blocks onto which more hydrophilic blocks are attached via bi-functional units, wherein the fixing film-forming polymer has at least two glass transition temperatures;
   (b) at least one thickening agent that is a cross-linked or non-cross-linked homopolymer or copolymer based on acrylic acid or methacrylic acid or acrylic and methacrylic acid, and
   (c) at least one co-thickening agent that is guar gum, wherein the composition has a viscosity of at least about 1.9 Pa·s.

14. The cosmetic composition according to claim 13, wherein:
   said at least one thickening agent is a cross-linked homopolymer based on acrylic acid.

15. The cosmetic composition according to claim 14, wherein the concentration of fixing film-forming polymer is between 0.1 and 10% by weight relative to the total weight of the composition, the concentration of thickening agent (b) is between 0.1 and 3% by weight relative to the total weight of the composition, and the concentration of the co-thickening agent (c) is between 0.05 and 2% by weight relative to the weight of the composition.

16. The cosmetic composition according to claim 14, wherein the concentration of fixing film-forming polymer is between 0.1 and 10% by weight relative to the total weight of the composition, the concentration of thickening agent (b) is between 0.2 and 2% by weight relative to the total weight of the composition, and the concentration of the co-thickening agent (c) is between 0.1 and 1% by weight relative to the total weight of the composition.

17. A method for the styling and fixing of hair, comprising applying to the hair a cosmetic composition comprising a cosmetically acceptable carrier containing:
   (a) at least one fixing film-forming polymer that is a branched block copolymer consisting essentially of 27.5 to 30.5 mol % of n-butyl acrylate, 26 to 36 mol % of acrylic acid, 33.3 to 45.3 mol % of methacrylic acid, and 0.48 to 0.92 mol % of allyl methacrylate, the polymer having a structure comprising hydrophobic blocks onto which more hydrophilic blocks are attached via bi-functional units,
   (b) at least one thickening agent that is a homopolymer or copolymer based on acrylic acid or methacrylic acid or acrylic and methacrylic acid that is cross-linked or non-cross-linked, and
   (c) at least one co-thickening agent that is guar gum, wherein the composition has a viscosity of at least about 1.9 Pa·s, wherein the fixing film-forming polymer has at least two glass transition temperatures.

18. The method according to claim 17, wherein said at least one thickening agent is a cross-linked homopolymer based on acrylic acid.

19. The method according to claim 18, wherein the concentration of fixing film-forming polymer is between 0.1 and 10% by weight relative to the total weight of the composition, the concentration of thickening agent (b) is between 0.1 and 3% by weight relative to the total weight of the composition, and the concentration of the co-thickening agent (c) is between 0.05 and 2% by weight relative to the total weight of the composition.

20. The method according to claim 18, wherein the concentration of fixing film-forming polymer is between 0.1 and 10% by weight relative to the total weight of the composition, the concentration of thickening agent (b) is between 0.2 and 2% by weight relative to the total weight of the composition, and the concentration of the co-thickening agent (c) is between 0.1 and 1% by weight relative to the total weight of the composition.

* * * * *